United States Patent
McGregor

(10) Patent No.: US 10,736,796 B2
(45) Date of Patent: Aug. 11, 2020

(54) RECLOSABLE FASTENER WITH INACTIVE REGIONS

(71) Applicant: 3M INNOVATIVE PROPERTIES COMPANY, St. Paul, MN (US)

(72) Inventor: Andrew J. McGregor, Minneapolis, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 695 days.

(21) Appl. No.: 15/507,339

(22) PCT Filed: Sep. 30, 2015

(86) PCT No.: PCT/US2015/053266
§ 371 (c)(1),
(2) Date: Feb. 28, 2017

(87) PCT Pub. No.: WO2016/057291
PCT Pub. Date: Apr. 14, 2016

(65) Prior Publication Data
US 2017/0281429 A1    Oct. 5, 2017

Related U.S. Application Data

(60) Provisional application No. 62/060,292, filed on Oct. 6, 2014.

(51) Int. Cl.
*A44B 18/00* (2006.01)
*A61F 13/58* (2006.01)
(Continued)

(52) U.S. Cl.
CPC ............ *A61F 13/581* (2013.01); *A41D 27/24* (2013.01); *A44B 18/0019* (2013.01);
(Continued)

(58) Field of Classification Search
CPC .. A44B 18/0073; A44B 18/0088; A41D 1/21; A41B 9/14
See application file for complete search history.

(56) References Cited

U.S. PATENT DOCUMENTS

| | | |
|---|---|---|
| 6,210,389 B1 | 4/2001 | Long |
| 7,416,545 B1 * | 8/2008 | Kline ...................... A61F 13/62 604/387 |
| 8,007,485 B2 * | 8/2011 | Popp .................. A44B 18/0003 428/99 |

FOREIGN PATENT DOCUMENTS

| | | |
|---|---|---|
| EP | 1021105 | 7/2000 |
| WO | WO 1999-03369 | 1/1999 |

(Continued)

OTHER PUBLICATIONS

International Search Report for PCT International Application No. PCT/US2015/053266, dated Dec. 14, 2015, 4 pages.

*Primary Examiner* — Tajash D Patel
(74) *Attorney, Agent, or Firm* — 3M Innovative Properties Company; Jonathan V. Sry

(57) ABSTRACT

At least one aspect of the present disclosure features a reclosable fastener for use on a non-woven article having a first part and a second part. The reclosable fastener includes a first fastener component, a second fastener component, and an adhesive layer attaching the second fastener component to the second part of the non-woven article. The first fastener component has first fastening elements. The first fastener component is attached to or integrated with the first part of the non-woven article. The second fastener component includes second fastening elements configured to engage with first fastening elements. The second fastener component includes one or more inactive regions. The second fastening elements within an inactive region are substantially deactivated.

18 Claims, 9 Drawing Sheets

(51) Int. Cl.
*A61F 13/62* (2006.01)
*A41D 27/24* (2006.01)
*B65D 33/20* (2006.01)
*B65D 65/14* (2006.01)
*B65D 33/16* (2006.01)

(52) U.S. Cl.
CPC ...... *A44B 18/0069* (2013.01); *A44B 18/0088* (2013.01); *A61F 13/62* (2013.01); *A61F 13/625* (2013.01); *B65D 33/20* (2013.01); *B65D 65/14* (2013.01); *A41D 2300/32* (2013.01); *B65D 33/1691* (2013.01)

(56) References Cited

FOREIGN PATENT DOCUMENTS

| | | |
|---|---|---|
| WO | WO 2001-43684 | 6/2001 |
| WO | WO 2007-047917 | 4/2007 |

* cited by examiner

RECLOSABLE FASTENER WITH INACTIVE REGIONS

CROSS REFERENCE TO RELATED APPLICATIONS

This application is a national stage filing under 35 U.S.C. 371 of PCT/US2015/053266, filed Sep. 30, 2015, which claims the benefit of U.S. Provisional Application No. 62/060,292, filed Oct. 6, 2014, the disclosure of which is incorporated by reference in its/their entirety herein.

TECHNICAL FIELD

The present disclosure is related to reclosable fastener with inactive regions.

SUMMARY

At least one aspect of the present disclosure features a reclosable fastener for use on a non-woven article having a first part and a second part. The reclosable fastener includes a first fastener component, a second fastener component, and an adhesive layer attaching the second fastener component to the second part of the non-woven article. The first fastener component has first fastening elements. The first fastener component is elongated and attached to or integrated with the first part of the non-woven article. The second fastener component comprises a plurality of second fastener segments. Each second fastener segment comprises second fastening elements configured to engage with first fastening elements. At least one of the plurality of second fastener segments comprises one or more inactive regions. The second fastening elements within an inactive region are substantially deactivated. A longitude axis of one of the one or more inactive regions is generally perpendicular to a longitude axis of the first fastener component.

At least one aspect of the present disclosure features a reclosable fastener for use on a non-woven article having a first part and a second part. The reclosable fastener includes a first fastener component, a second fastener component, and an adhesive layer attaching the second fastener component to the second part of the non-woven article. The first fastener component comprises first fastening elements. The first fastener component is attached to or integrated with the first part of the non-woven article. The second fastener component comprises a plurality of second fastener segments. Each second fastener segment comprises second fastening elements configured to engage with first fastening elements. At least one of the plurality of second fastener segments has a peripheral and includes a continuously closed inactive region along the peripheral. The second fastening elements within the inactive region are substantially deactivated.

At least one aspect of the present disclosure features a garment having an opening with a first side and a second side relative to the opening. The garment includes a first fastener component, a second fastener component, and an adhesive layer attaching the second fastener component along the second side of the garment. The first fastener component includes first fastening elements. The first fastener component is attached to or integrated with the garment along peripheral of the first side. The second fastener component comprises a plurality of second fastener segments. Each second fastener segment comprises second fastening elements configured to engage with first fastening elements. At least one of the plurality of second fastener segments comprises one or more inactive regions. The second fastening elements within an inactive region are substantially deactivated.

BRIEF DESCRIPTION OF DRAWINGS

The accompanying drawings are incorporated in and constitute a part of this specification and, together with the description, explain the advantages and principles of the invention. In the drawings.

DETAILED DESCRIPTION

Figure 1:
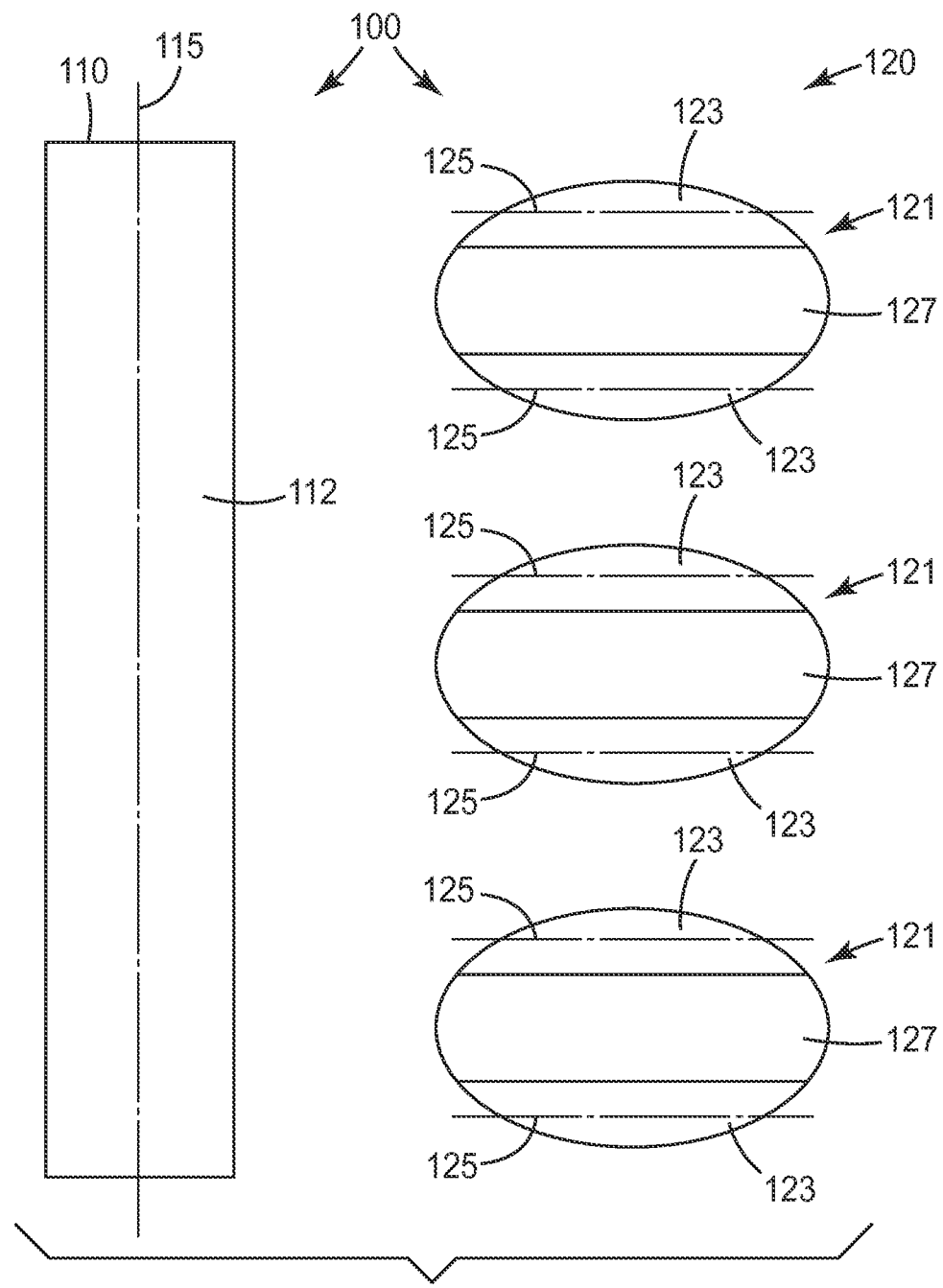
FIG. 1 illustrates one embodiment of a reclosable fastener with inactive region(s)

Reclosable fastener has been used widely in garments, diapers, and other articles. For a fastener including two fastener components, fastening elements of the two fastener components are engaged with each other to create a bonding force between the components. In some cases, the reclosable fastener is attached to a non-woven article with limited attachment force. For example, the reclosable fastener is attached to a non-woven article by adhesive. In such cases, the reclosable fastener can be designed to include inactive regions in one or both of the fastener components to reduce the bonding force between these components. In some specific cases, the bonding force at the peripheral of the fastener needs to be reduced, because the fastener tends to be detached from the non-woven article at the peripheral. At least some aspects of the present disclosure are directed to a reclosable fastener with one or more inactive regions. Fastening elements in an inactive region are substantially deactivated. In some embodiments, the inactive regions are designed to be disposed at locations selected to reduce bonding force between two fastening components at the locations.

In some embodiments, reclosable fastener with inactive regions can be used on a garment. In some cases, the garment is a disposable garment. The disposable garment may use non-woven materials. The garment can have an opening with two sides, where each side can be integrated with or attached to fastener components. In some cases, the material used in the non-woven article or the garment is easy to be torn when operated with reclosable fasteners, or is easy to be separated from the reclosable fastener attached thereon; one or more inactive regions in the fastener component can reduce the bonding force between the fastener components, thereby preventing the failure mode of one or more fasteners being separated from the non-woven article or garment.

In some cases, a garment can be a convective device with at least one convective apparatus attached to or integrated with the garment. A garment can be a clinical garment used to temporarily clothe a patient in a clinical setting. Such garments include hospital gowns, robes, bibs and other equivalents. The clinical setting may be a medical or dental office or clinic, a hospital, or any facility or institution that provides medical or dental treatment to patients. A convective device receives and distributes at least one stream of inflating medium in a structure for being disposed on, adjacent, or next to the core and/or the limbs of a body. The convective device can distribute inflating medium to regulate temperature using, for example, warm air or cool air.

When pressurized with warmed air, a convective apparatus emits warmed air through one or more of its surfaces. The emission of inflating medium can be through mechanical openings for example, holes, apertures, interstices, slits and the like; or using air permeable materials. The convective device may also operate with pressurized air at ambient temperature or cooled, pressurized air. Moreover, it may be useful to operate the device with pressurized air that includes a mixture of selected constituents including water vapor, medicaments, scented compounds, and the like.

FIG. 1 illustrates one embodiment of a reclosable fastener 100 with inactive region(s). The reclosable fastener 100 includes two fastener components 110 and 120. The fastener component 120 includes a plurality of fastener segments 121. Each fastener segment 121 includes one or more inactive regions 123 and active regions 127. The fastener component 110 includes fastening elements (not shown in FIG. 1) to engage with fastening elements (not shown in FIG. 1) of the fastener component 120. For example, the fastener component 110 includes loop elements and the fastener component 120 includes hook elements to engage with the loop elements. As another example, the fastener component 110 and the fastener component 120 include interlocking elements engaging with each other, for example, 3M™ Dual Lock™ Reclosable Fasteners.

The fastening elements in the inactive regions 123 are substantially deactivated, where a portion of fastening elements in the inactive regions 123 are deactivated. In some cases, 80% or more fastening elements in the inactive regions 123 are deactivated. In some other cases, 50% or more fastening elements in the inactive regions 123 are deactivated. In some implementations, an inactive area has less than 50% of the engagement strength of an active area with fully activated fastening elements. Fastening elements can be deactivated by mechanical approaches, heating, or the like, for example, crushed, deformed, or flattened during manufacturing process of the fasteners. In some implementations, the manufacturing process can use a roller which flattens the fastening elements or in the cutting die having a feature to flatten the elements. In some cases, the roller may be heated to achieve the desired amount of deactivation. In some implementations, the deactivation can also be achieved by removing the elements by shearing or cutting. The fastening elements may also be deactivated by not capping the element stems during the initial manufacturing process.

The fastener component 110 has a longitude axis 115. An inactive region 123 has a longitude axis 125. In the example illustrated, the longitude axis 115 is generally perpendicular to the longitude axis 125. In one embodiment, each fastener component 110 is corresponding to more than one fastener segments 121.

Figure 2A:
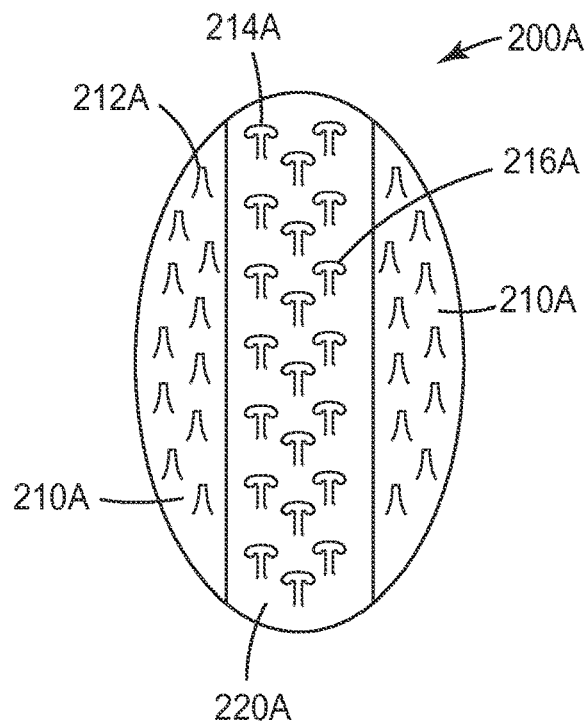
FIGS. 2A and 2B illustrate some example of a fastener component with inactive regions.
Figure 2B:
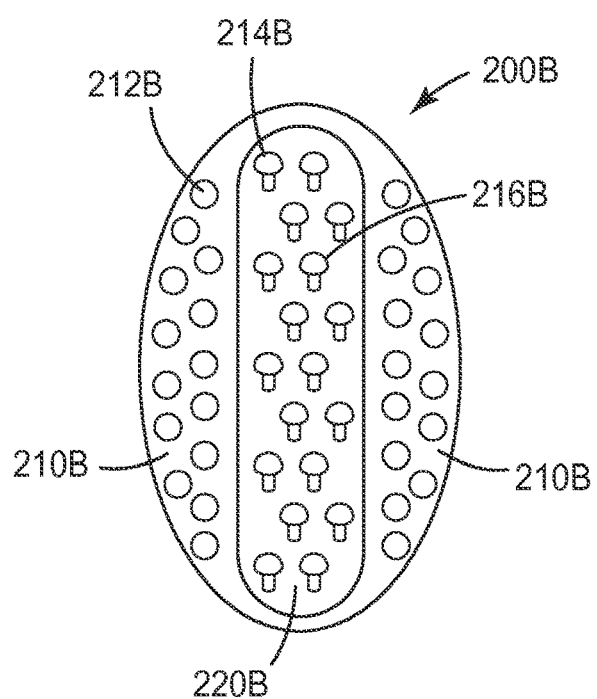

FIGS. 2A and 2B illustrate some examples of a fastener component with inactive regions. As illustrated in FIG. 2A, the fastener component 200A includes two inactive regions 210A and one active region 220A proximate at the center. The fastener component 200A is in a generally oval shape. A majority of or all fastening elements 214A in the active region 220A have engaging members 216A. In comparison, a majority of or all fastening elements 212A in the inactive region 210A do not have engaging member. The two inactive regions 210A are disposed generally parallel to each other. The two inactive regions are disposed proximate to the peripheral of the fastener component.

As illustrated in FIG. 2B, the fastener component 200B includes an inactive region 210B along the peripheral of the fastener component 200B, which is a closed shape. The inactive region 210B surrounds the active region 220B. A majority of or all fastening elements 214B in the active region 220B have engaging members 216B. In comparison, a majority of or all fastening elements 212B in the inactive region 210B do not have engaging member.

Figure 3A:
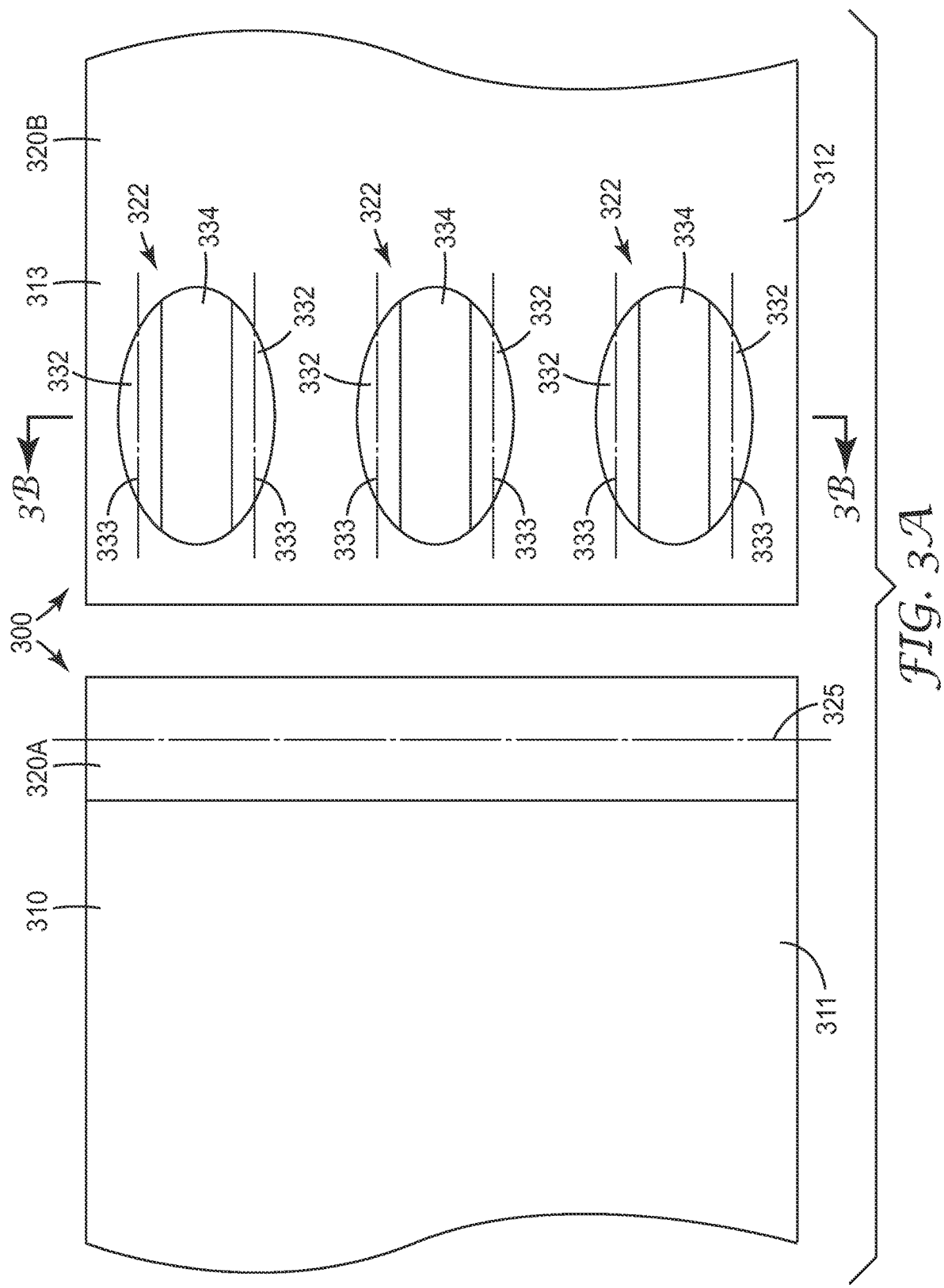
FIG. 3A illustrates a top plane view of one embodiment of a reclosable fastener for use on a non-woven article.
Figure 3B:
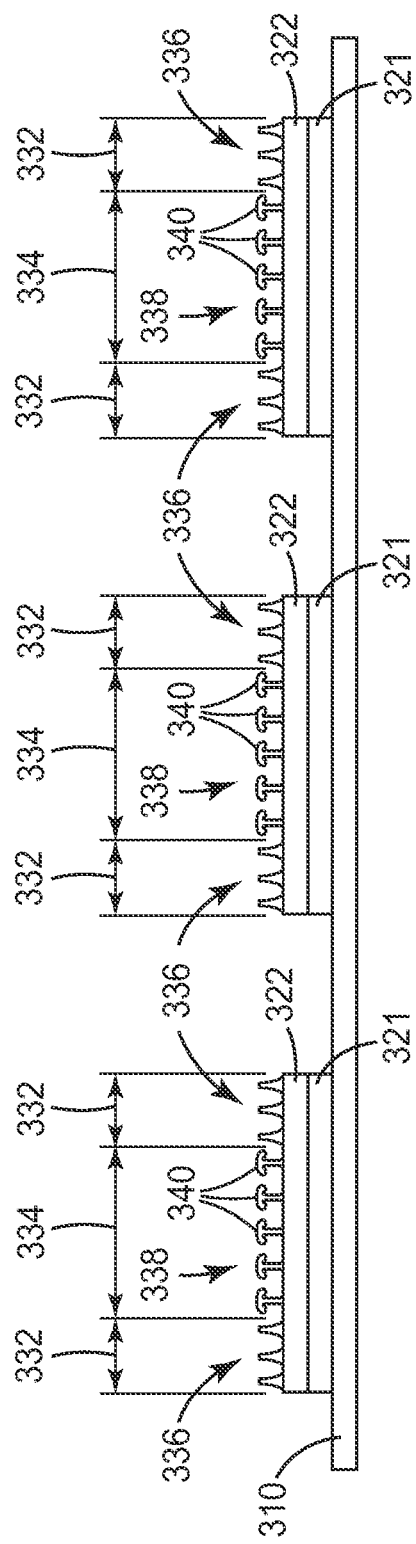
FIG. 3B illustrate a schematic cross-sectional view of the second fastener component illustrated in FIG. 3A.

FIG. 3A illustrates a top plane view of one embodiment of a reclosable fastener 300 for use on a non-woven article 310. The non-woven article 310 has a first part 311 and a second part 312. The reclosable fastener 300 includes a first fastener component 320A and a second fastener component 320B. FIG. 3B illustrate a schematic cross-sectional view of the second fastener component illustrated in FIG. 3A. The first fastener component 320A includes first fastening elements. As illustrated, the first fastener component 320A is elongated and attached to or integrated with the first part 311 of the non-woven article 310.

The second fastener component 320B includes a plurality of second fastener segments 322. Each second fastener segment 322 includes second fastening elements configured to engage with first fastening elements. At least some of the second fastener segments 322 include one or more inactive regions 332 and active regions 334, where the second fastening elements within an inactive region 332 are substantially deactivated. In one embodiment, the longitude axis 333 of the inactive regions 332 is generally perpendicular to a longitude axis 325 of the first fastener component 320A. As illustrated in FIG. 3B, an adhesive layer 321 attaching the second fastener segments 322 to the second part 312 of the non-woven article 310. Further, the fastening elements 338 in the active regions 334 have engaging members 340. At least some of the fastening elements 336 in the inactive regions 332 do not have engaging members.

In some embodiments, at least some of the second fastener segments 322 are discretely disposed. In an example, each of the plurality of second fastener segments is in a generally oval shape. In some implementations, the first fastener component 320A includes a loop component and the second fastener component 320B includes a hook component. In some cases, the first fastener component 320A includes a plurality of first fastener segments. In some configurations, one of the plurality of first fastener segments is corresponding to one or more second fastener segments. In some implementations, the first and/or second fastener component includes interlocking components, for example, 3M™ Dual Lock™ Reclosable Fasteners.

Figure 4A:
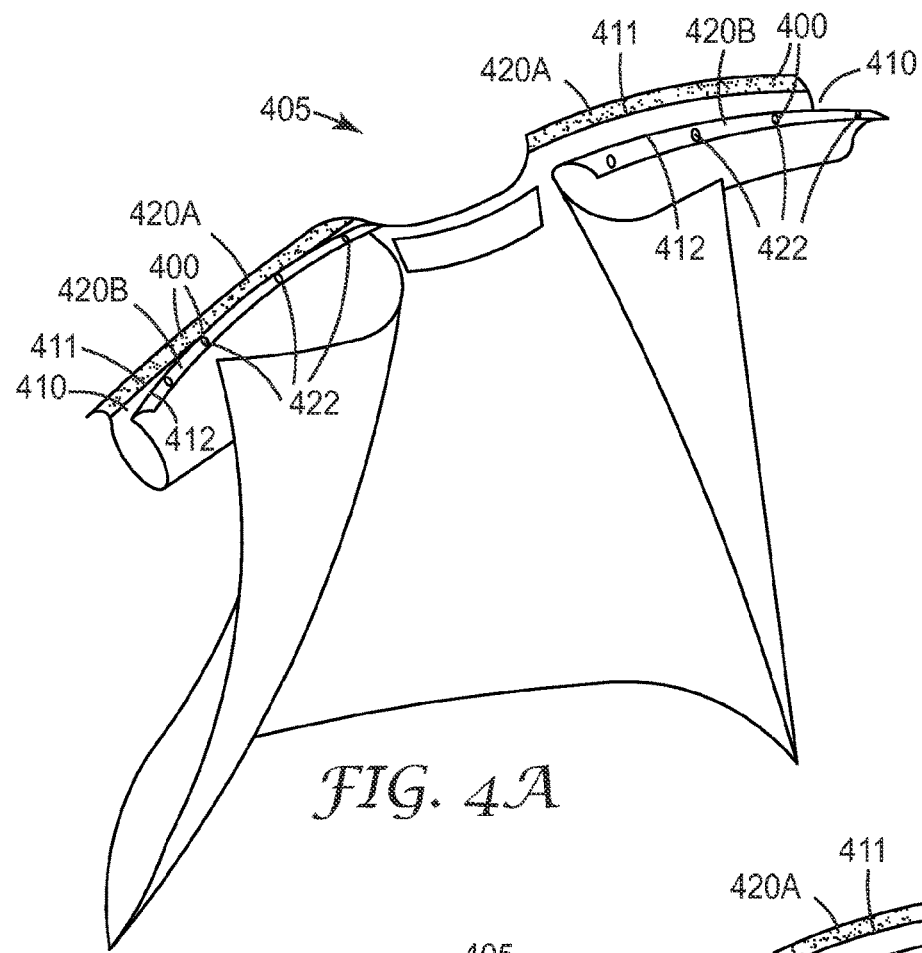
FIG. 4A illustrates one embodiment of a garment using a reclosable fastener.

FIG. 4A illustrates one embodiment of a garment 405 using a reclosable fastener 400. The garment 405 has an opening 410 with a first side 411 and a second side 412 relative to the opening 410. The reclosable fastener 400 is used along the opening 410. The reclosable fastener 400 can use any fastener design described herein. In one embodiment, the reclosable fastener 400 includes a first fastener component 420A and a second fastener component 420B. The first fastener component 420A, having a plurality of first fastening elements (not illustrated), is attached to or integrated with the garment along the peripheral of the first side 411. The second fastener component 420B includes a plurality of second fastener segments 422. Each second fastener segment 422 has a plurality of second fastening elements (not illustrated) configured to engage with first fastening elements. At least some of the second fastener segments 422 have one or more inactive regions, where the second fastening elements within an inactive region are substantially deactivated. An adhesive layer, similar to the adhesive layer 321 illustrated in FIG. 3B, is used to attach the second fastener component 422 along the second side 412 of the garment 405.

Figure 4B:
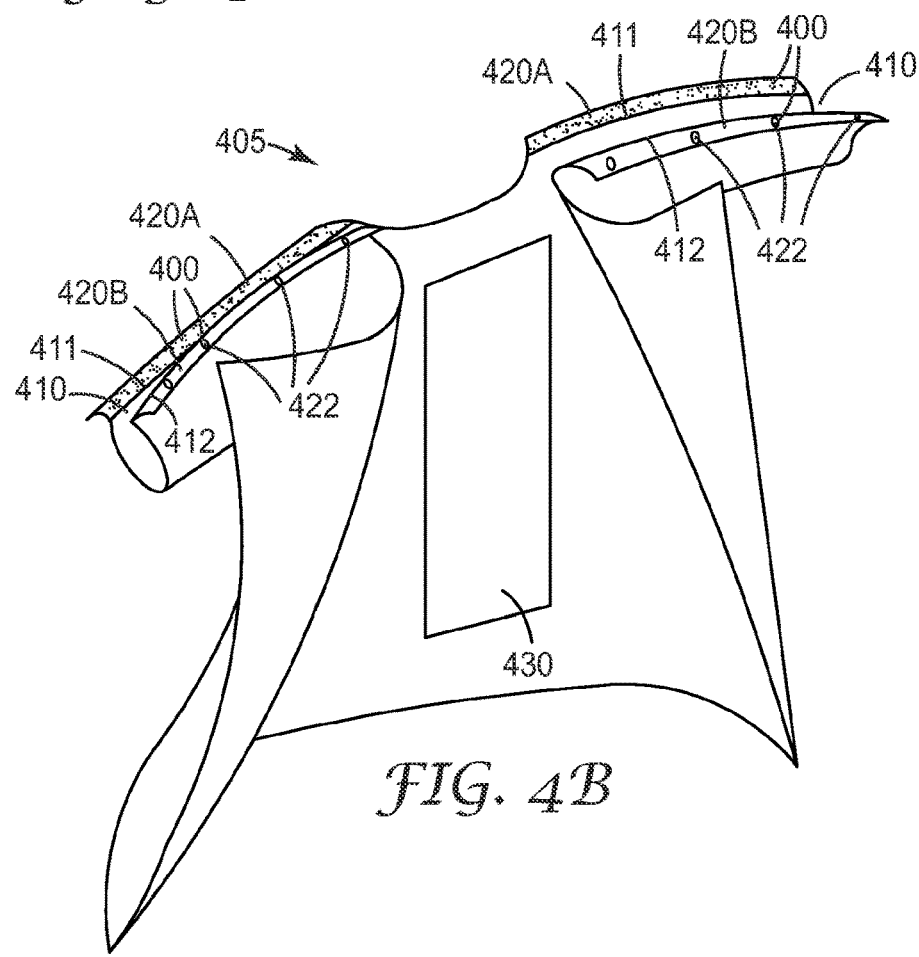
FIG. 4B illustrates a garment with a convective device using a reclosable fastener.

FIG. 4B illustrates a garment 405 with a convective device 430 using a reclosable fastener. In one embodiment, the convective device 430 can have a standalone inflatable structure, typically including two or more sheets of materials bonded together at periphery. In another embodiment, the convective device 430 can have an inflatable structure integrated with the garment. In some cases, the convective device 430 is releasbily attached to the garment 405 via an attachment device. The attachment device includes, for example, fasteners, adhesive, hook and loop, snaps, or the like.

Figure 5A:
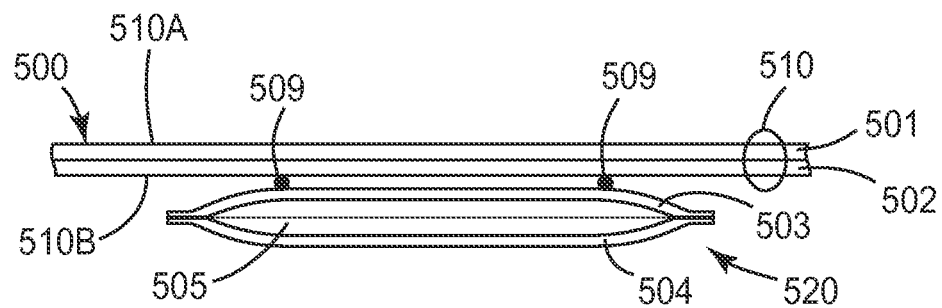
FIGS. 5A and 5B are cross-sectional views of two embodiments of a convective device attached to or integrated with a garment.
Figure 5B:
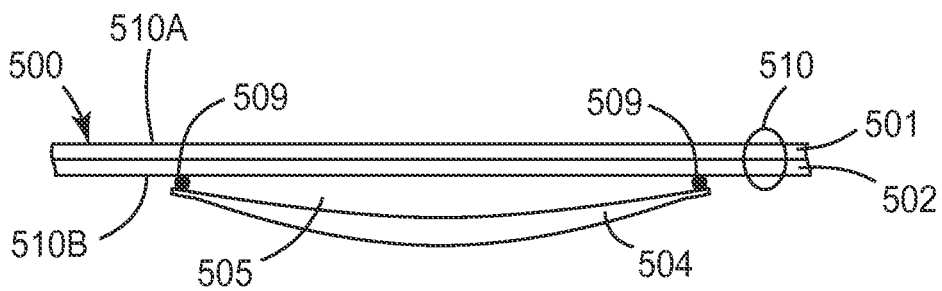

FIGS. 5A and 5B are cross-sectional views of two embodiments of a convective device 500 that is attached to or integrated with a garment. As illustrated in FIG. 5A, the convective device 500 includes a garment sheet 510, a material sheet 503, a base sheet 504, and an attachment device 509. In some cases, at least one of the sheets can be made from a polyolefin non-woven extrusion coated, each with a coating of polypropylene on one side. In some other cases, at least one of the sheets can be poly lactic acid spunbond with polyolefin based extrusion coat. Each of the sheets 510, 503, and 504 may have one or more layers. For example, the garment sheet 510 may include two layers, a top layer 501 and a bottom layer 502. In some cases, the base sheet 504 is air permeable and the material sheet 503 is not air permeable. An air permeable sheet can be air permeable via mechanical structures, for examples, having openings formed by punching, slitting, or cutting, or via material property. The material sheet 503 is attached to a surface of the base sheet 504 to form an inflatable portion. The attachment device 509 can use any permanent or releasable attachment means, for example, two-sided adhesive, perforated tear-away tabs, hook and loop, sewing, snaps, heat, ultrasonic, rivets, repositionable adhesives, mechanical reclosable fasteners, or the like. In some cases, at least some portions of the garment sheet 510 has a first garment surface 510A and a second garment surface 510B that have different friction coefficients from each other.

Alternatively, as illustrated in FIG. 5B, the convective device 500 includes a garment sheet 510, a base sheet 504, and an attachment device 509. In such embodiment, the garment sheet 510 is not air permeable and the base sheet 504 is air permeable. The garment sheet 510 is attached to a surface of the base sheet 504 to form an inflatable portion by the attachment device 509.

Figure 6A:
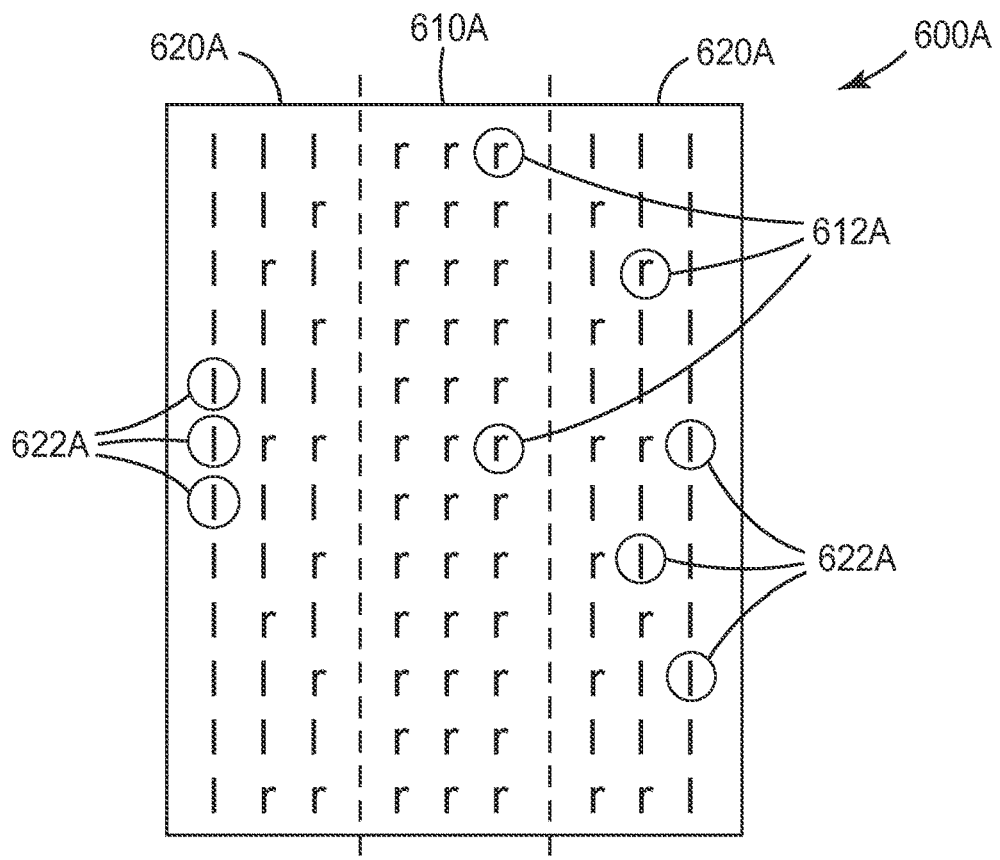
FIGS. 6A-6F illustrate some examples of reclosable fasteners with inactive region(s)

FIGS. 6A-6F illustrate some examples of reclosable fasteners with peripheral inactive region(s). People skilled in the art should readily design similar fasteners with inactive regions. FIG. 6A illustrates a fastener 600A having active region 610A and inactive regions 620A. The fastening elements in the active region 610A include mostly or all fastening elements 612A with engaging members. The fastening elements in the inactive region 620A include some fastening elements 612A with engaging members and mostly fastening elements 622A without engaging members. In one embodiment as illustrated, the inactive region 620A has a higher percentage of deactivated fastening elements getting close to the edge. For example, the inactive region 620A has all deactivated fastening elements at the edge row; the inactive region 620A has three deactivated fastening elements out of every four fastening elements at the row next to the edge row; and the inactive region 620A has one deactivated fastening elements out of every two fastening elements at the next row.

Figure 6B:
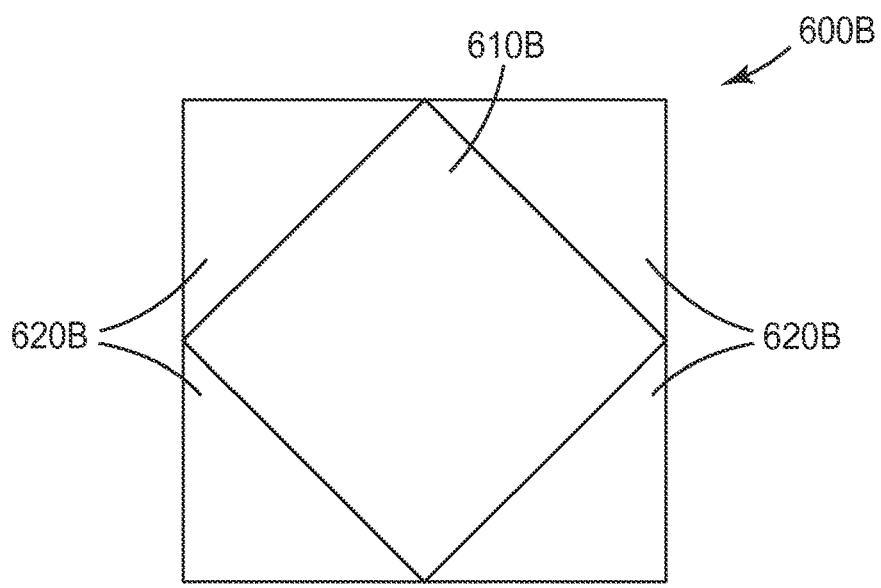
Figure 6C:
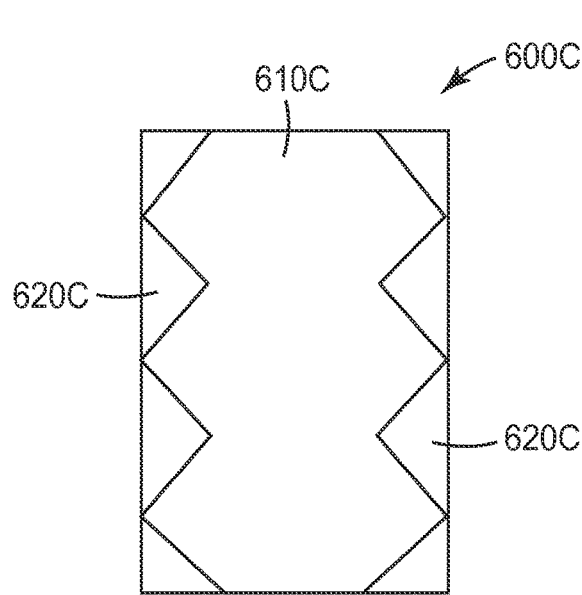

FIG. 6B illustrates a fastener 600B in a generally rectangular shape. The fastener 600B includes a diamond shape active region 610B surrounded by inactive regions 620B. The fastening elements in the inactive regions 620B are substantially deactivated (i.e., most fastening elements having no engaging members). FIG. 6C illustrates a fastener 600C in a generally rectangular shape. The fastener 600C includes an active region 610C surrounded by inactive regions 620C. The inactive regions 620C are in a generally saw-tooth shape. The fastening elements in the inactive regions 620C are substantially deactivated.

Figure 6D:
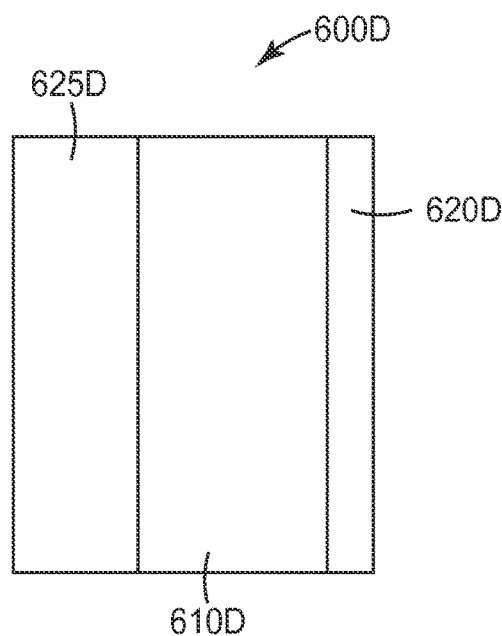
Figure 6E:
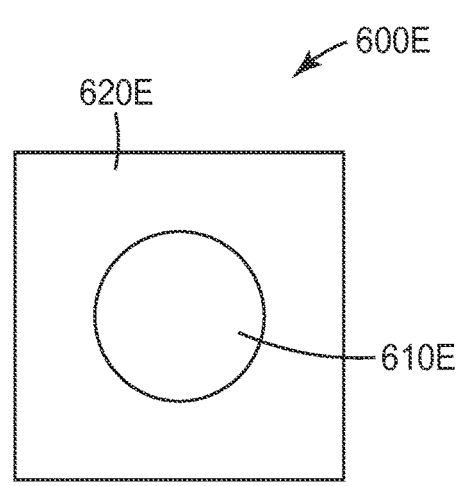
Figure 6F:
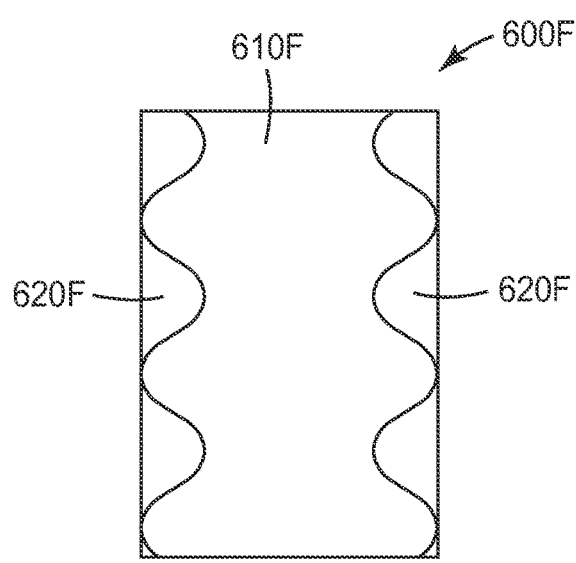

FIG. 6D illustrates a fastener 600D in a generally rectangular shape. The fastener 600D includes an active region 610D and inactive regions 620D and 625D. The fastening elements in the inactive regions are substantially deactivated. The inactive regions 620D and 625D have different size and/or shape. FIG. 6E illustrates a fastener 600E in a generally rectangular shape. The fastener 600E includes an active region 610E surrounded by an inactive region 620E. The active region 610E is in a generally round or oval shape. The fastening elements in the inactive regions are substantially deactivated. FIG. 6F illustrates a fastener 600F in a generally rectangular shape. The fastener 600F includes an active region 610F surrounded by inactive regions 620F. The fastening elements in the inactive regions are substantially deactivated. The inactive region 620F has a wavy or sinusoidal boundary.

Figure 7A:
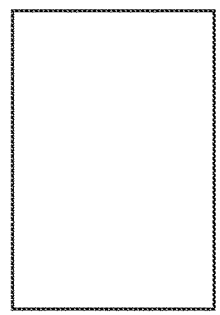
FIGS. 7A-7F illustrate some examples of different shapes of reclosable fastener components.
Figure 7B:
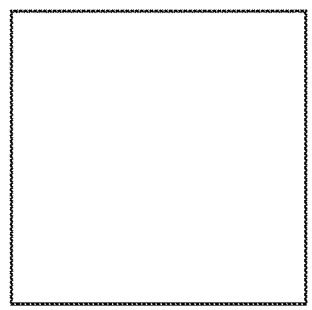
Figure 7C:
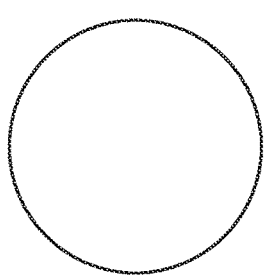
Figure 7D:
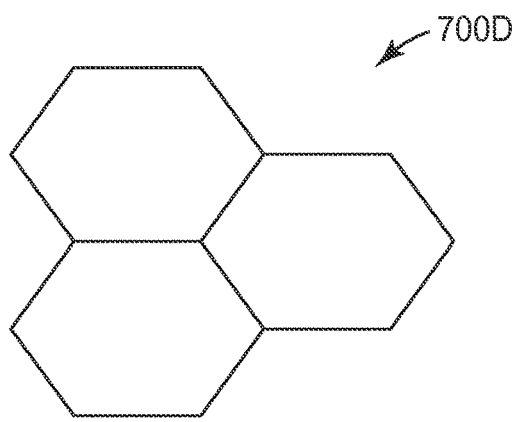
Figure 7E:
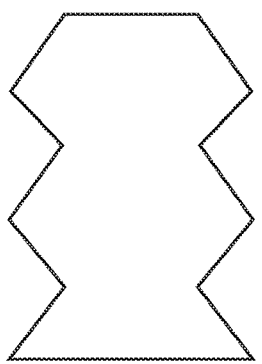
Figure 7F:
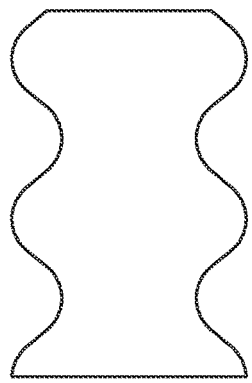

FIGS. 7A-7F illustrate some examples of different shapes of reclosable fastener components. Various shapes of reclosable fastener components can be paired together. For example, a rectangular reclosable fastener component can be paired with a saw-tooth shaped reclosable fastener component. As another example, a number of rectangular fastener components can be paired with an elongated generally rectangular fastener component. As yet another example, a number of fastener components with different shapes can be paired with an elongated generally rectangular fastener component. For a reclosable fastener with two or more components, at least one of the components can have inactive region(s). FIG. 7A illustrates an example of a reclosable fastener component 700A in a generally rectangular shape. FIG. 7B illustrates an example of a reclosable fastener component 700B in a generally square shape. FIG. 7C illustrates an example of a reclosable fastener component 700C in a generally round shape. FIG. 7D illustrates an example of a reclosable fastener component 700D in a generally hexagon shape. In some cases as illustrated in FIG. 7D, multiple fastener components can be arranged and disposed together. FIG. 7E illustrates an example of a reclosable fastener component 700E in a generally saw-tooth shape. FIG. 7F illustrates an example of a reclosable fastener component 700F with a wavy edge.

Exemplary Embodiments

Embodiment 1. A reclosable fastener for use on a non-woven article having a first part and a second part, comprising: a first fastener component comprising first fastening elements, wherein the first fastener component is elongated and attached to or integrated with the first part of the non-woven article, a second fastener component comprising a plurality of second fastener segments, each second fastener segment comprising second fastening elements configured to engage with first fastening elements, at least one of the plurality of second fastener segments comprising one or more inactive regions, wherein the second fastening elements within an inactive region are substantially deactivated, and wherein a longitude axis of one of the one or more inactive regions is generally perpendicular to a longitude axis of the first fastener component, and an adhesive layer attaching the second fastener component to the second part of the non-woven article.

Embodiment 2. The reclosable fastener of Embodiment 1, wherein two of the inactive regions are disposed generally parallel to each other.

Embodiment 3. The reclosable fastener of Embodiment 1 or 2, wherein at least two of the plurality of second fastener segments are discretely disposed.

Embodiment 4. The reclosable fastener of any of Embodiment 1-3, wherein each of the plurality of second fastener segments is in a generally rectangular shape.

Embodiment 5. The reclosable fastener of any of Embodiment 1-4, wherein at least one of the one or more inactive regions is disposed proximate to the edge of a second fastener segment.

Embodiment 6. The reclosable fastener of any of Embodiment 1-5, wherein the first fastener component includes a loop component.

Embodiment 7. The reclosable fastener of Embodiment 6, wherein the second fastener component includes a hook component.

Embodiment 8. The reclosable fastener of any of Embodiment 1-7, wherein the first fastener component includes a plurality of first fastener segments.

Embodiment 9. The reclosable fastener of Embodiment 8, wherein one of the plurality of first fastener segments is corresponding to one or more of the plurality of second fastener segments.

Embodiment 10. The reclosable fastener of any of Embodiment 1-9, wherein the first and/or second fastener component includes an interlocking component.

Embodiment 11. A reclosable fastener for use on a non-woven article having a first part and a second part, comprising: a first fastener component comprising first fastening elements, wherein the first fastener component is attached to or integrated with the first part of the non-woven article, a second fastener component comprising a plurality of second fastener segments, each second fastener segment comprising second fastening elements configured to engage with first fastening elements, at least one of the plurality of second fastener segments having a peripheral and comprising a continuously closed inactive region along the peripheral, wherein the second fastening elements within the inactive region are substantially deactivated, and an adhesive layer attaching the second fastener component to the second part of the non-woven article.

Embodiment 12. The reclosable fastener of Embodiment 11, wherein at least two of the plurality of second fastener segments are discretely disposed.

Embodiment 13. The reclosable fastener of Embodiment 11 or 12, wherein each of the plurality of second fastener segments is in a generally rectangular shape.

Embodiment 14. The reclosable fastener of any of Embodiment 11-13, wherein the first fastener component includes a loop component.

Embodiment 15. The reclosable fastener of Embodiment 14, wherein the second fastener component includes a hook component.

Embodiment 16. The reclosable fastener of any of Embodiment 11-15, wherein the first fastener component includes a plurality of first fastener segments.

Embodiment 17. The reclosable fastener of Embodiment 16, wherein one of the plurality of first fastener segments is corresponding to one or more of the plurality of second fastener segments.

Embodiment 18. The reclosable fastener of any of Embodiment 11-17, wherein the first and/or second fastener component includes an interlocking component.

Embodiment 19. A garment having an opening with a first side and a second side relative to the opening, comprising: a first fastener component comprising first fastening elements, wherein the first fastener component is attached to or integrated with the garment along peripheral of the first side, a second fastener component comprising a plurality of second fastener segments, each second fastener segment comprising second fastening elements configured to engage with first fastening elements, at least one of the plurality of second fastener segments comprising one or more inactive regions, wherein the second fastening elements within an inactive region are substantially deactivated, and an adhesive layer attaching the second fastener component along the second side of the garment.

Embodiment 20. The garment of Embodiment 19, wherein the garment is a disposable garment.

Embodiment 21. The garment of Embodiment 19 or 20, wherein the garment uses a non-woven material.

Embodiment 22. The garment of any of Embodiment 19-21, wherein a longitude axis of one of the one or more inactive regions is generally perpendicular to a longitude axis of the first fastener component.

Embodiment 23. The garment of Embodiment 22, wherein two of the one or more inactive regions are disposed generally parallel to each other.

Embodiment 24. The garment of any of Embodiment 19-23, wherein at least one of the plurality of second fastener segments has a peripheral and comprises a continuously closed inactive region along the peripheral.

Embodiment 25. The garment of any of Embodiment 19-24, wherein at least two of the plurality of second fastener segments are discretely disposed.

Embodiment 26. The garment of any of Embodiment 19-25, wherein each of the plurality of second fastener segments is in a generally rectangular shape.

Embodiment 27. The garment of any of Embodiment 19-26, wherein at least one of the one or more inactive regions is disposed proximate to the edge of a second fastener segment.

Embodiment 28. The garment of any of Embodiment 19-27, wherein the first fastener component includes a loop component.

Embodiment 29. The garment of Embodiment 28, wherein the second fastener component includes a hook component.

Embodiment 30. The garment of any of Embodiment 19-29, wherein the first fastener component includes a plurality of first fastener segments.

Embodiment 31. The garment of Embodiment 30, wherein one of the plurality of first fastener segments is corresponding to one or more of the plurality of second fastener segments.

Embodiment 32. The garment of any of Embodiment 19-31, wherein the first and/or second fastener component includes an interlocking component.

The present invention should not be considered limited to the particular examples and embodiments described above, as such embodiments are described in detail to facilitate explanation of various aspects of the invention. Rather the present invention should be understood to cover all aspects of the invention, including various modifications, equivalent processes, and alternative devices and materials falling within the spirit and scope of the invention as defined by the appended claims.

What is claimed is:

1. A reclosable fastener for use on a non-woven article having a first part and a second part, comprising:
    a first fastener component comprising first fastening elements, wherein the first fastener component is elongated and attached to or integrated with the first part of the non-woven article,
    a second fastener component comprising a plurality of second fastener segments, each second fastener segment comprising second fastening elements configured to engage with first fastening elements, at least one of the plurality of second fastener segments comprising one or more inactive regions and one or more active regions, wherein the second fastening elements within an inactive region are substantially deactivated, and wherein a longitude axis of one of the one or more inactive regions is generally perpendicular to a longitude axis of the first fastener component, and
    an adhesive layer attaching the second fastener component to the second part of the non-woven article,
    wherein at least two of the one or more inactive regions or the one or more active regions of the plurality of second fastener segments are discretely disposed.

2. The reclosable fastener of claim 1, wherein two of the inactive regions are disposed generally parallel to each other.

3. The reclosable fastener of claim 1, wherein each of the plurality of second fastener segments is in a generally rectangular shape.

4. The reclosable fastener of claim 1, wherein at least one of the one or more inactive regions is disposed proximate to the edge of a second fastener segment.

5. The reclosable fastener of claim 1, wherein the first fastener component includes a plurality of first fastener segments.

6. A reclosable fastener for use on a non-woven article having a first part and a second part, comprising:
    a first fastener component comprising first fastening elements, wherein the first fastener component is attached to or integrated with the first part of the non-woven article,
    a second fastener component comprising a plurality of second fastener segments, each second fastener segment comprising second fastening elements configured to engage with first fastening elements, at least one of the plurality of second fastener segments having a peripheral and comprising continuously closed inactive regions along the peripheral and comprising one or more active regions, wherein the second fastening elements within the inactive region are substantially deactivated, and
    an adhesive layer attaching the second fastener component to the second part of the non-woven article,
    wherein the inactive regions or the one or more active regions of the plurality of second fastener segments are discretely disposed.

7. The reclosable fastener of claim 6, wherein the first and/or second fastener component includes an interlocking component.

8. A garment having an opening with a first side and a second side relative to the opening, comprising:
    a first fastener component comprising first fastening elements, wherein the first fastener component is attached to or integrated with the garment along peripheral of the first side,
    a second fastener component comprising a plurality of second fastener segments, each second fastener segment comprising second fastening elements configured to engage with first fastening elements, at least one of the plurality of second fastener segments comprising one or more inactive regions and one or more active regions, wherein the second fastening elements within an inactive region are substantially deactivated, and
    an adhesive layer attaching the second fastener component along the second side of the garment, wherein the garment uses a non-woven material,
    wherein at least two of the one or more inactive regions or the one or more active regions of the plurality of second fastener segments are discretely disposed.

9. The garment of claim 8, wherein the garment is a disposable garment.

10. The garment of claim 8, wherein two of the one or more inactive regions are disposed generally parallel to each other.

11. The garment of claim 8, wherein at least one of the plurality of second fastener segments has a peripheral and comprises a continuously closed inactive region along the peripheral.

12. The garment of claim 8, wherein at least one of the one or more inactive regions is disposed proximate to the edge of a second fastener segment.

13. The garment of claim 8, wherein a longitude axis of one of the one or more inactive regions is generally perpendicular to a longitude axis of the first fastener component.

14. The garment of claim 8, wherein the first fastener component includes a loop component.

15. The garment of claim 14, wherein the second fastener component includes a hook component.

16. The garment of claim 8, wherein the first fastener component includes a plurality of first fastener segments.

17. The garment of claim 16, wherein one of the plurality of first fastener segments is corresponding to one or more of the plurality of second fastener segments.

18. The reclosable fastener of claim 6, wherein the one or more active regions are surrounded by the inactive regions.

* * * * *